(12) United States Patent
Jeon et al.

(10) Patent No.: US 9,492,446 B2
(45) Date of Patent: Nov. 15, 2016

(54) MANUFACTURING METHOD OF SOLID DISPERSION CONTAINING ITRACONAZOLE

(75) Inventors: Hong-Ryeol Jeon, Gyeonggi-Do (KR); Se-Geun Yu, Gyeonggi-do (KR); Bong-Sang Lee, Gyeonggi-Do (KR); Se-Heum Oh, Gyeonggi-Do (KR); Jeong-Seo Park, Gyeonggi-Do (KR); Dong-Ryun Oh, Gyeonggi-do (KR); Do-Woo Kwon, Chungcheongnam-do (KR)

(73) Assignees: CTC BIO, Inc., Seoul (KR); Hong-Ryeol Jeon, Suwon, Gyeonggi-do (KR)

(*) Notice: Subject to any disclaimer, the term of this patent is extended or adjusted under 35 U.S.C. 154(b) by 2282 days.

(21) Appl. No.: 11/630,781

(22) PCT Filed: Jun. 24, 2005

(86) PCT No.: PCT/KR2005/001991
§ 371 (c)(1),
(2), (4) Date: May 31, 2009

(87) PCT Pub. No.: WO2006/001669
PCT Pub. Date: Jan. 5, 2006

(65) Prior Publication Data
US 2009/0298847 A1    Dec. 3, 2009

(30) Foreign Application Priority Data

Jun. 24, 2004   (KR) .................. 10-2004-0047369

(51) Int. Cl.
*A61K 31/496*   (2006.01)
*A61K 31/10*    (2006.01)
*A61K 9/14*     (2006.01)

(52) U.S. Cl.
CPC ............. *A61K 31/496* (2013.01); *A61K 9/146* (2013.01)

(58) Field of Classification Search
USPC ...................................... 514/183
See application file for complete search history.

(56) References Cited

U.S. PATENT DOCUMENTS 5,883,097 A *  3/1999  Lovey et al. ............ 514/254.07
6,039,981 A *  3/2000  Woo et al. ................... 424/601
2003/0185888 A1* 10/2003  Wong et al. ................. 424/473

FOREIGN PATENT DOCUMENTS

KR   2001-098419      11/2001
WO   WO-0197853       12/2001
WO   WO-2004/004683    1/2004

OTHER PUBLICATIONS

Jung et al., "Enhanced solubility and dissolution rate of itraconazole by a solid dispersion technique," International Journal of Pharmaceutics vol. 187, Issue 2, 5 Oct. 1999, pp. 209-218.*
English machine translation of KR 2001098419, published 2001.*
Fresta, et al. "Poly-d,1-Lactic Acid Nanospheres as a Drug Delivery System of Antifungal Drugs", *Acta Technologiae et Legis Medicamenti*, vol. XII, No. 2, (2001).
Wang, et al. "Study of the Phase Behavior of Polyethylene Glycol 6000-Itraconazole Solid Dispersions Using DSC", *International Journal of Pharmaceutics*, vol. 272(1-2), p. 181-187 (2004).
Verreck, et al. "Characterization of Solid Dispersions of Itraconazole and Hydroxypropylmethylcellulose Prepared by Melt Extrusion—Part I", *International Journal of Pharmaceutics*, vol. 251(1-2), p. 165-174 (2003).
Six, et al., "Increased Physical Stability and Improved Dissolution Properties of Itraconazole, a Class II Drug, by Solid Dispersions that Combine Fast-and Slow-Dissolving Polymers", *Journal of Pharmaceutical Sciences*, vol. 93, No. 1 (Jan. 15, 2004).

* cited by examiner

*Primary Examiner* — Kortney L Klinkel
*Assistant Examiner* — William Lee
(74) *Attorney, Agent, or Firm* — Mintz Levin Cohn Ferris Glovsky and Popeo, P.C.; Kongsik Kim; Elaine V. Morlock

(57) ABSTRACT

The present invention relates to a method for preparing an itraconazole-containing solid dispersion. The itraconazole-containing solid dispersion according to the preparing method of the present invention has both improved solubility and rapid dissolution rate so that it has an excellent bioavailability. The itraconazole-containing solid dispersion of the present invention is also independent of pH variation of human stomach so that it can minimize the absorption variation of intra- and inter-individuals. In addition, the itraconazole-containing solid dispersion according to the preparing method of the present invention is stable for a long time. The present invention also provides an economical and environment-friendly method for manufacturing an itraconazole-containing composition because the method adds a lactic acid in a solution comprising itraconazole to decrease the amount of an organic solvent needed to dissolve itraconazole.

6 Claims, 1 Drawing Sheet

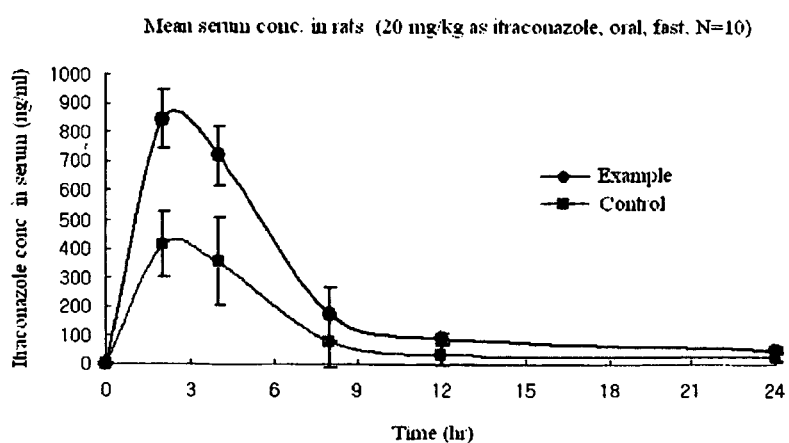

MANUFACTURING METHOD OF SOLID DISPERSION CONTAINING ITRACONAZOLE

TECHNICAL FIELD

The present invention relates to a method for preparing an itraconazole-containing solid dispersion.

BACKGROUND ART

Itraconazole, a weak basic drug (pKa=3.7), is little soluble in water so that its bioavailability is low. Itraconazole has the low water-solubility of less than 1 ug/ml even if its solubility increases in lower pH solution (See PCT publication No. WO 01/85,135). It is well known that a rate-determining step for absorption of a poorly water-soluble drug like itraconazole largely depends on the drug's solubility and dissolution rate. Even if such a drug disintegrates completely, the drug does not dissolve in a small volume of body fluid because of its low solubility, which results in a reduced bioavailability (See pharmaceutics, hanrimwon, South Korea, p. 218).

Moreover, the solubility of some commercially available formulations containing itraconazole falls rapidly with a small increase of pH. The solubility difference between pH 1.6 and 2.4 reaches to 5.3 times (See PCT publication No. WO 01/85,135). Thus, the pH-dependence of the commercial itraconazole formulations may cause inter- and intra-individual absorption variation. For example, as for AIDS patients having a higher pH in stomach because of their poor gastric secretion, their absorption of itraconazole was reported to be no more than 50% of that of normal people (See The pharmacokinetics of oral itraconazole in AIDS patients, J. Pharm. Pharmacol., 44, 1992, p. 618). Therefore, it has been recommended to take an itraconazole formulation with a drink like a COLA that can decrease the pH of stomach. It has also been recommended to take it after meal because the higher pH of stomach before meal may reduce its absorption.

In addition, when considering that human stomach has a normal pH range of about 1 to 3.5 and the pH of stomach of almost 16% adults is over 3, a drug formulation that decreases the solubility variation in the above pH range can enlarge the absorption of itraconazole and reduce the inter- and intra-individual absorption variation (See The design and evaluation of controlled release systems for the gastrointestinal tract, In advances in drug delivery systems, Amsterdam, 1986, p. 27-38). That is, a composition (formulation) that can increase itraconazole's solubility and prevent a decrease of solubility in the normal pH range of human stomach should be designed in order to achieve an improved bioavailability of itraconazole.

Furthermore, because the pH of human intestine is over 5, an itraconazole passing stomach without being absorbed will precipitate rapidly. This decrease of solubility may cause poor absorption and low bioavailability (See Drug delivery system, hanrimwon, Seoul, South Korea, p. 28-31). Based on this problem, the rapid dissolution of itraconazole before reaching an intestine (that is, increasing the dissolution rate of formulation) is one of important factors to improve bioavailability of an itraconazole composition.

Because of the above reasons, bioavailabilities of oral itraconazole formulations are very low and absorption variations are large depending on stomach condition of each individual including food and disease.

To solve these problems, PCT patent publication No. WO 85/02767 and U.S. Pat. No. 4,767,604 disclosed methods trying to improve the solubility and bioavailability of itraconazole by forming a complex with cyclodextrin and its derivatives. However, the method has demerits that the solubility of inclusion materials (cyclodextrin and its derivatives) decreases depending on a used solvent and it has limits such as a large manufacturing cost and the large amount and size of one preparation inevitably caused by inclusion ratio.

PCT patent publication No. WO 97/44,014 also discloses solid dispersions comprising itraconazole and a water-soluble polymer made by a melt-extrusion process in order to increase the dissolution rate and bioavailability of itraconazole. However, keeping a fixed temperature for melting drug and polymer and blocking the happening of amorphous or crystal form are difficult, which makes it difficult to control the quality of the formulation. Avoiding the change of formulation property and the happening of carbide is also difficult because of the above reasons.

PCT patent publication No. WO 94/05,236 also discloses a capsule having beads made by a process comprising: making a solution comprising itraconazole and a hydrophilic polymer, for example, hydroxypropylmethylcellulose; spray-drying the solution to coat sugar spheres of some size determined on the basis of aggregation and surface area; and re-coating the coated sugar spheres with polyethyleneglycol to make a sealing film. However, the beads may show a big difference of absorption according to stomach conditions of each individual (for example, pH and stomach retention time) and have a disadvantage that their manufacturing process is very complex. Furthermore, the process needs a large amount of organic solvent (for example, methylene chloride) to dissolve itraconazole in a spraying solution, which increases manufacturing time and make the total process cost-ineffective.

PCT patent publication No. WO 99/33,467 also discloses a method for preparing solid dispersions comprising: dissolving itraconazole and a pH-dependent hydrophilic polymer in a solvent; and spray-drying the solution to make a solid dispersion. The method can increase the solubility of itraconazole to some degree and reduce the variation caused by food intake, but it is not cost-effective because the method needs a large amount of organic solvent to dissolve itraconazole and it needs much time to spray-dry such a large amount of organic solvent. In addition, considering the pH of over 3 in stomach as described above, the solubility of the pH-dependent polymer itself may decrease in such a pH and it results in the decrease of the dissolution rate of itraconazole (See PCT publication No. WO 01/85,135).

Besides the above methods for manufacturing an itraconazole formulation with an improved solubility and rapid dissolution rate, there are many methods like vacuum-melting methods, spray-drying methods and solvent-evaporating methods. However, most methods have problems like bad yield, large manufacturing cost, long manufacturing time, complexity of process and content decrease during process.

DISCLOSURE OF INVENTION

Technical Problem

Accordingly, an object of the present invention is to provide a method for preparing an itraconazole-containing solid dispersion that has improved water-solubility and rapid dissolution rate, pH-independence (that is, has the low variation of inter- and intra-individuals according to pH of stomach) and improved bioavailability.

Another object of the present invention is to provide a method for preparing an itraconazole-containing solid dispersion that is environment-friendly and cost-effective.

Technical Solution

To achieve the objects, the present invention is to provide a method for preparing an itraconazole-containing solid dispersion comprising: preparing a solution in which itraconazole, polymer and lactic acid are dissolved; and drying the solution.

Preferably, the present invention is to provide said method wherein the polymer is at least one selected from the group consisting of alkylcellulose, hydroxyalkylcellulose, carboxyalkylcellulose, polyvinylalcohol, polyvinylpyrrolidone, polyvinylacetate, polyalkene oxide, polyalkene glycol, polyethylene-polypropylene copolymer, polyoxyethylene-polyoxypropylene copolymer, zein, shellac, diethylaminoacetate, aminoalkylmethacrylate copolymer, sodium alginate, chitosan and its derivatives, gelatin, gum and poly-L-lysine.

More preferably, the present invention is to provide said method wherein the polymer is used in the range of 0.43 parts by weight based on the weight of itraconazole.

More preferably, the present invention is to provide said method wherein the lactic acid is used in the range of 0.2-5 parts by weight based on the weight of itraconazole.

Preferably, the present invention is to provide said method wherein the solution further comprises a solubilizer. More preferably, the present invention is to provide said method wherein the solubilizer is used in the range of 0.1-3 parts by weight based on the weight of itraconazole.

Preferably, the present invention is to provide said method wherein the solution further comprises a solid-phase acid. More preferably, the present invention is to provide said method wherein the solid-phase acid is at least one selected from the group consisting of citric acid, tartaric acid, maleic acid and succinic acid.

Preferably, the present invention is to provide said method wherein the solution is prepared with at least one solvent selected from the group consisting of water, dichloromethane, ethanol, methanol, chloroform and acetone. More preferably, the present invention is to provide said method wherein the solvent comprises water of between 2 and 15 (w/w) % by the weight of the total solvent.

The present invention also provides an itraconazole-containing solid dispersion made by the methods described above.

An itraconazole-containing solid dispersion prepared by the methods of the present invention has remarkably improved solubility and dissolution rate and these solubility and dissolution rate are pH-independent because itraconazole and lactic acid are minutely mixed and mixedly present between polymers. The preparing method of the present invention is also environment-friendly and cost-effective because it does not need a large amount of organic solvent to dissolve itraconazole by adding lactic acid in a spray-drying solution.

The preparing method and solid dispersion of the present invention will be described in detail below.

The preparing method of the present invention uses a polymer that can be dissolved and dried (for example, spray-dried) with itraconazole, thereby being able to form a solid dispersion. The polymer of the present invention includes, but is not limited to, methylcellulose, ethylcellulose, hydroxymethylcellulose, hydroxyethylcellulose, hydroxyethylmethylcellulose, hydroxypropylmethylcellulose, carboxymethylcellulose, polyvinylalcohol, polyvinylpyrrolidone, polyvinylacetate, polyalkene oxide, polyalkene glycol, polyethylene-polypropylene copolymer, polyoxyethylene-polyoxypropylene copolymer (for example, Poloxamer™), zein, shellac, diethyllaminoacetate (for example, AEA™), aminoalkylmethacrylate copolymer (for example, Eudragit E™), sodium alginate, chitosan and its derivatives, gelatin, gum, poly-L-lysine and their mixture. These polymers improve solubility and dissolution rate of itraconazole and delay the change of itraconazole from amorphous to crystal form by forming a solid dispersion with itraconazole. The delay may play a role in preventing the re-decrease of the improved solubility over time.

Preferably, the polymer of the present invention is used in the range of 0.2-10 parts by weight based on the weight of itraconazole. More preferably, the polymer is used in the range of 0.4-3 parts by weight. If the used amount of the polymer is less than the above range, re-crystallization may happen so that the improved solubility re-decreases. If the used amount of the polymer is more than the above range, the high viscosity of the spray-drying solution will make the manufacturing process difficult and the viscosity of the solid dispersion may delay itraconazole's dissolution, and the amount and size of one tablet also increase, which weakens patient's compliance.

The lactic acid of the present invention raises the solubility of itraconazole, which decreases the required amount of organic solvent to dissolve itraconazole. The resulting decrease of the amount of spray-drying solution shortens spraying time and decreases manufacturing cost. The lactic acid of the present invention is minutely mixed and mixedly present with itraconazole between polymers, which is believed to make the micro-environment surrounding itraconazole acidic. This acidic micro-environment is thought to increase the solubility of itraconazole in stomach and reduce the variation of the solubility according to pH of stomach.

The present inventors investigated many acids. However, most acids except some acids are difficult to form a solid dispersion and some in such acids did not increase the solubility of itraconazole and were dependent on the change of pH. Some solid dispersions using some acids were too unstable to commercialize. However, itraconazole-containing solid dispersions using lactic acid easily overcame the above-described limitations.

More specifically, butyric acid, fumaric acid, phosphoric acid and hydrochloric acid are difficult to use because of their bad odor and toxicity. Alginic acid and chitic acid are difficult to deal with and dry (particularly, spray-dry) because of the high viscosity of spray-drying solution when their amount used are over 3 w/w % by the total weight of the solid dispersion. Moreover, a solid dispersion using any one selected from the group consisting of phosphoric acid, hydrochloric acid, ascorbic acid, malic acid, succinic acid, hippuric acid, propionic acid, butyric acid, chitic acid, fumaric acid, cholic acid, alginic acid and so on did not show a desirable increase of dissolution rate.

Preferably, the lactic acid of the present invention is used in the range of 0.2-5 parts by weight based on the weight of itraconazole. If the used amount of lactic acid is less than 0.2 parts by weight, the increase of the dissolution rate is not desirable. If the used amount of lactic acid is more than 5 parts by weight, selecting an appropriate solvent for drying is difficult and aggregates of the solid dispersion may be formed.

When dissolving about 1:1 weight ratio mixture of itraconazole and polymer in a solvent (for example, dichloromethane), the solvent without lactic acid needs about 2.8 times amount of solvent to dissolve them than the solvent comprising about ⅓ parts by weight of lactic acid based on the weight of itraconazole. This result means that using solvent without lactic acid needs about 400 liters of dichloromethane for making a spray-drying solution containing 100 kg of itraconazole, whereas using solvent with lactic acid needs only about 140 liters of dichloromethane. This reduction can also decrease manufacturing cost and shorten time for manufacturing.

In addition to the economic merits, this reduction of organic solvent will be helpful to environmental and regulatory aspects that want to decrease the amount used for manufacturing a product.

Itraconazole-containing solid dispersions using lactic acid and polymer are more stable in the aspect of re-crystallization than solid dispersion using only polymer, which is expected to be caused by the property of lactic acid acting as a desiccant absorbing water. The dissolution rates of itraconazole-containing solid dispersions without lactic acid more easily decreased than the solid dispersion of the present invention on both a long-term storage test and an accelerated stability test.

The lactic acid of the present invention also blocks the decrease of the solubility of a pH-dependent polymer itself like aminoalkylmethacrylate copolymer or diethyllaminoacetate that is more soluble in lower pH when the pH of in vivo circumstance increases, which can obstruct the decrease of solubility and dissolution rate of the solid dispersion of the present invention, and is expected to play an important role in the decrease of the inter- and intra-individual variation of bioavailability.

The solvent for dissolving itraconazole, polymer and lactic acid in the present invention includes, but is not limited to, water, dichloromethane, chloroform, ethanol, methanol, acetone and their mixture. Preferably, the solvent comprises water of between 1 and 20 w/w % by the weight of the total solvent, more preferably, water of between 2 and 15 w/w % in order to prevent a precipitation of used lactic acid and adequately act as an acidifier described above.

The present inventors also discovered that if the solvent further comprises a solubilizer, the above-described objects of the present invention can be more easily achieved. Particularly, the added solubilizer may increase solubility and dissolution rate of itraconazole in various stomach situations so that it can reduce the variation of solubility depending on pH of stomach. The effect of solubilizer depends on the type of polymer. The solid dispersion using a pH-dependent polymer like diethylaminoacetate or aminoalkylmethacrylate copolymer is not relatively influenced by adding a solubilizer, whereas the solubility variation of the solid dispersion using a pH-independent polymer according to pH variation are largely reduced. The solubilizer of the present invention can also reduce a needed amount of organic solvent to dissolve itraconazole like lactic acid.

The solubilizer that can be used in the present invention includes, but is not limited to, propylene carbonate, diethyleneglycol monoethylether, dimethyl isosorbide, polyoxyethyleneglycolated natural castor oil, polyoxyethyleneglycolated hydrogenated castor oil, HCORTM™ (Nikkol), oleic acid ester derivatives, GELUCIRE™, caprylic monoglyceride, caprylic diglyceride, caprylic acid monoglyceride, caprylic acid diglyceride, sorbitan fatty acid ester derivatives, SOLUTOL™ and their mixture. Preferably, the solubilizer is used in the range of 0.1-3 parts by weight on the weight of itraconazole.

The present invention also provides a method for preparing a itraconazole-containing solid dispersion comprising: making a solution in which itraconazole, polymer, lactic acid and solid phase acid; and drying the solution.

General processes (for example, capsule filling and tabletting) for preparing a tablet or capsule comprising the solid dispersion of the present invention may be difficult because the melting point of lactic acid is relatively low. For example, tabletting the mixture of pharmaceutically acceptable excipients and the solid dispersion comprising itraconazole, polymer and lactic acid may cause tabletting problems like sticking and capping, which can be prevented by adding a large amount of lubricant. However, it causes the increase of the amount and size of one tablet, which may decrease patient's compliance.

Accordingly, preferably, the solid dispersion of the present invention further comprises a solid-phase acid that can improve the bioavailability of itraconazole to some extent and handling property. Nevertheless, preferably, the solid-phase acid should be used in the range of less than 1 part by weight based on the weight of lactic acid in order not to reduce the above-described effect of the present invention.

More preferably, the solid-phase acid of the present invention is at least one selected from the group consisting of citric acid, tartaric acid, maleic acid and succinic acid. These solid-phase acids have both some solubility-improving effect and good physical properties.

The present invention also provides itraconazole-containing pharmaceutical compositions comprising a solid dispersion of the present invention and a pharmaceutically acceptable excipient (for example, disintegrator, diluent, lubricant and flavor) for make a oral preparation like tablet, powder, granule, capsule and so on.

For example, the disintegrator includes, but is not limited to, lactose, starch, sodium starch glycolate, crospovidone, croscarmellose sodium, maltodextrin and their mixture.

For example, the diluent includes, but is not limited to, starch, sorbitol, mannitol, sucrose, colloidal silica, spray-dried lactose, lactose anhydrous, calcium dihydrogen phosphate, calcium phosphate dibasic anhydrous, microcrystalline cellulose and their mixture. The diluent may be added to a itraconazole-containing solid dispersion to make a tablet, capsule or granule, and may be added in a solid dispersion with itraconazole during a process using a spray-dryer or a fluidized bed granulator for making the solid dispersion.

The lubricant is used to give a good free flowability during capsule filling and packing of powder, granule and pellet, or to prevent tabletting problems like sticking and capping. Suitable lubricants include, but are not limited to, colloidal silica, talc, magnesium stearate and their mixture.

A machine for drying a solution comprising itraconazole of the present invention includes, but is not limited to, drying oven, spray-dryer, fluidized bed granulator and C/F granulator. A process using a spray-dryer comprises: dissolving itraconazole, polymer and lactic acid in a suitable solvent; dispersing talc, magnesium stearate, colloidal silica or their mixture in the solution; and spray-drying the final liquid.

PCT patent publication No. WO 98/42,318, WO 94/05, 263 and WO 01/85,135 disclose that many factors like spraying-pressure, spraying-velocity, viscosity of spraying solution and some temperature settings of the spray-dryer may change the dissolution rate of the final product and cause a manufacturing problem. It is also reported that the size of sugar sphere and the spraying conditions are seriously limited because of surface size, remaining organic solvents and happening of agglomerates.

However, the dissolution characteristics of an itraconazole-containing solid dispersion of the present invention are not easily changed according to spraying conditions and the size of sugar sphere. The difference of dissolution pattern according to the size of the solid dispersion particle of the present invention is not shown, and the difference of dissolution pattern is also not shown even when using the agglomerates of the solid dispersion of the present invention. This means that the solid dispersion of the present invention is uniform because the lactic acid used in dissolving itraconazole and polymer can improve the uniformity of ingredients in solution and thus solid dispersion. The solid dispersion using this uniform solution can show a regular dissolution pattern bearing no relation to the size of particle. This means that adding lactic acid in a spray-drying solution is helpful to keeping uniformity of the solid dispersion of itraconazole.

A process using a fluidized bed granulator comprises: making a solution in which itraconazole, polymer, lactic acid and so on are dissolved; fluidizing disintegrator, diluent, colloidal silica, light anhydrous silicic acid or their mixture in a chamber of the fluidized bed granulator; spraying the solution on the fluidized ingredients. The method using the fluidized bed granulator does not also easily change the dissolution pattern of the solid dispersion of the present invention according to viscosity of the solution, spraying velocity, a amount of inlet air, temperature of inlet air and outlet air, particle size of the solid dispersion like the method using the spray-dryer. The process using the fluidized bed granulator can be easily applied to tablet, capsule or granule by changing ingredients like diluents fluidized in a chamber.

ADVANTAGEOUS EFFECTS

An itraconazole-containing solid dispersion made by the method of the present invention has an improved bioavailability, reduced variation in intra- and inter-individuals, and good stability. That is, the present invention provides a method for preparing an itraconazole-containing solid dispersion that can release itraconazole without change according to stomach condition of a individual (for example, dietary condition, food and disease) because its solubility and dissolution rate are not changed in extensive pH range. The method of the present invention is environment-friendly and economical because it can reduce a required amount of organic solvent by adding lactic acid in the solvent for improving itraconazole's solubility.

BRIEF DESCRIPTION OF THE DRAWINGS

FIG. 1 shows a mean serum concentration of itraconazole in rats. An itraconazole-containing solid dispersion prepared according to a example of the present invention and a commercially available preparation (Sporanox™, Janssen) are administered orally.

MODE FOR THE INVENTION

Hereinafter, a preferred embodiment of the present invention will be described in detail. Prior to the description, it should be understood that various modifications are possible to the embodiments of the present invention, and it should be understood that the scope of the invention is not limited to the following embodiments. The embodiments are purposed to merely give better explanation of the invention to those ordinarily skilled in the art.

EXAMPLE 1

Selection of Acid

EXAMPLE 1-1

Using Phosphoric Acid as an Acidifying Agent 100 g of itraconazole, 100 g of aminoalkylmethacrylate copolymer (polymer) and 50 g of phosphoric acid were dissolved in a mixture of ethanol:dichloromethane (1:1(v/v), 360 g) and water (40 g) for making a spray-drying solution. Sodium starch glycolate (80 g) and colloidal silica (80 g) were fluidized in a chamber of a fluidized bed granulator (GX20, Freund, Japan) and then the spraying-drying solution was sprayed to prepare a itraconazole-containing solid dispersion. The preparing condition was as follows:
temperature of inlet air: 40-70° C.
temperature of outlet air: 30-50° C.
temperature of the solid dispersion: 25-40° C.
speed of revolution of rotor: 150-300 rpm
spraying velocity: 15-40 ml/min
pressure in the chamber: −2.5-0 kpa
drying time after making the solid dispersion: 10-30 min
speed of revolution of rotor during drying: 50-200 rpm
pressure in the chamber during chamber: −3.0-0 kpa

EXAMPLE 1-2-EXAMPLE 1-13

Several solid dispersions were made using other acids shown in table 1 instead of phosphoric acid like example 1-1. Hydrochloric acid, ascorbic acid, malic acid, lactic acid, succinic acid, hippuric acid, chitic acid, propionic acid, butyric acid, fumaric acid, alginic acid and cholic acid were used in example 1-2, example 1-3, example 1-4, example 1-5, example 1-6, example 1-7, example 1-8, example 1-9, example 1-10, example 1-11, example 1-12 and example 1-13, respectively.

EXPERIMENTAL EXAMPLE 1

Dissolution Test According to the Kind of Acid

Itraconazole-containing capsules (100 mg of itraconazole in 450 mg of the total contents) were prepared with any one of the solid dispersions made in example 1 and a 3:1(w/w) mixture of sodium starch glycolate and colloidal silica, and then subjected to dissolution tests [paddle (100 rpm), pH 3.0 buffer solution (dissolution medium), 30 minutes (dissolution time)] to evaluate the effect of the kind of acid. Results were shown in table 1.

TABLE 1

| Example | Acid | Dissolution rate (%) | Easiness of preparing |
|---|---|---|---|
| Example 1-1 | Phosphoric acid | 45.3 | X |
| Example 1-2 | Hydrochoric acid | 37.0 | X |
| Example 1-3 | Ascorbic acid | 25.3 | |
| Example 1-4 | Malic acid | 42.2 | |
| Example 1-5 | Lactic acid | 89.7 | |
| Example 1-6 | Succinic acid | 30.1 | |
| Example 1-7 | Hippuric acid | 15.9 | |
| Example 1-8 | Chitic acid | 60.8 | X |
| Example 1-9 | Propionic acid | 20.4 | X |
| Example 1-10 | Butyric acid | 25.7 | X |

TABLE 1-continued

| Example | Acid | Dissolution rate (%) | Easiness of preparing |
|---|---|---|---|
| Example 1-11 | Fumaric acid | 18.6 | X |
| Example 1-12 | Alginic acid | 11.3 | X |
| Example 1-13 | Choric acid | 33.0 | |

"X" of table 1 means that process is difficult because of bad odor of acid, toxicity of acid or viscosity of spraying solution.

As shown in table 1, the solid dispersion using lactic acid had a much higher dissolution rate than the solid dispersions using other acids.

EXAMPLE 2

Evaluating the Effect of Lactic Acid when Using Aminoalkylmethacrylate Copolymer as a Polymer

EXAMPLE 2-1

100 g of itraconazole and 100 g of aminoalkylmethacrylate copolymer (polymer) were dissolved in ethanol:dichloromethane (1:1(v/v), 1,200 g) to make a spraying solution. Sodium starch glycolate (105 g) and colloidal silica (105 g) were fluidized in a chamber of a fluidized bed granulator and then the spraying-solution was sprayed to prepare a itraconazole-containing solid dispersion. Conditions of the fluidized bed granulator were the same as in example 1-1.

EXAMPLE 2-2

100 g of itraconazole, 100 g of aminoalkylmethacrylate copolymer and 50 g of lactic acid were dissolved in a mixture of ethanol:dichloromethane (1:1(v/v), 360 g) and water (40 g) to make a spraying solution. The remaining processes and conditions were the same as in example 2-1.

EXAMPLE 2-3

100 g of itraconazole, 100 g of aminoalkylmethacrylate copolymer, 50 g of lactic acid and 30 g of diethylene glycol monoethyl ether (solubilizer) were dissolved in a mixture of ethanol:dichloromethane (1:1(v/v), 360 g) and water (40 g) to make a spraying solution. The remaining processes and conditions were the same as in example 2-1.

EXAMPLE 2-4

100 g of itraconazole, 100 g of aminoalkylmethacrylate copolymer, 50 g of lactic acid, 30 g of diethylene glycol monoethyl ether (solubilizer), 105 g of sodium starch glycolate and 105 g of colloidal silica were mixed to make a mixture containing itraconazole.

EXAMPLE 3

Evaluating the Effect of Lactic Acid when Using Hydroxyproylmethylcellulose as a Polymer

EXAMPLE 3-1

100 g of itraconazole and 100 g of hydroxyproylmethylcellulose (polymer) were dissolved in ethanol:dichloromethane (1:1(v/v), 1,200 g) to make a spraying solution. The remaining processes and conditions were the same as in example 2-1.

EXAMPLE 3-2

100 g of itraconazole, 100 g of hydroxyproylmethylcellulose and 50 g of lactic acid were dissolved in a mixture of ethanol:dichloromethane (1:1(v/v), 360 g) and water (40 g) to make a spraying solution. The remaining processes and conditions were the same as in example 2-1.

EXAMPLE 3-3

100 g of itraconazole, 100 g of hydroxyproylmethylcellulose, 50 g of lactic acid and 30 g of diethylene glycol monoethyl ether (solubilizer) were dissolved in a mixture of ethanol:dichloromethane (1:1(v/v), 360 g) and water (40 g) to make a spraying solution. The remaining processes and conditions were the same as in example 2-1.

EXAMPLE 3-4

100 g of itraconazole, 100 g of hydroxyproylmethylcellulose, 50 g of lactic acid, 30 g of diethylene glycol monoethyl ether (solubilizer), 105 g of sodium starch glycolate and 105 g of colloidal silica were mixed to make a mixture containing itraconazole.

EXAMPLE 4

Evaluating the Effect of Lactic Acid when Using Polyvinylpyrrolidone as a Polymer

EXAMPLE 4-1

100 g of itraconazole and 100 g of polyvinylpyrrolidone (polymer) were dissolved in ethanol:dichloromethane (1:1 (v/v), 1,200 g) to make a spraying solution. The remaining processes and conditions were the same as in example 2-1.

EXAMPLE 4-2

100 g of itraconazole, 100 g of polyvinylpyrrolidone and 50 g of lactic acid were dissolved in a mixture of ethanol:dichloromethane (1:1(v/v), 360 g) and water (40 g) to make a spraying solution. The remaining processes and conditions were the same as in example 2-1.

EXAMPLE 4-3

100 g of itraconazole, 100 g of polyvinylpyrrolidone, 50 g of lactic acid and 30 g of diethylene glycol monoethyl ether (solubilizer) were dissolved in a mixture of ethanol:dichloromethane (1:1(v/v), 360 g) and water (40 g) to make a spraying solution. The remaining processes and conditions were the same as in example 2-1.

EXAMPLE 4-4

100 g of itraconazole, 100 g of polyvinylpyrrolidone, 50 g of lactic acid, 30 g of diethylene glycol monoethyl ether (solubilizer), 105 g of sodium starch glycolate and 105 g of colloidal silica were mixed to make a mixture containing itraconazole.

EXAMPLE 5

Evaluating the Effect of Lactic Acid when Using Polyvinylalcohol as a Polymer

EXAMPLE 5-1

100 g of itraconazole and 100 g of polyvinylalcohol (polymer) were dissolved in ethanol:dichloromethane (1:1 (v/v), 1,200 g) to make a spraying solution. The remaining processes and conditions were the same as in example 2-1.

EXAMPLE 5-2

100 g of itraconazole, 100 g of polyvinylalcohol and 50 g of lactic acid were dissolved in a mixture of ethanol:dichloromethane (1:1(v/v), 360 g) and water (40 g) to make a spraying solution. The remaining processes and conditions were the same as in example 2-1.

EXAMPLE 5-3

100 g of itraconazole, 100 g of polyvinylalcohol, 50 g of lactic acid and 30 g of diethylene glycol monoethyl ether (solubilizer) were dissolved in a mixture of ethanol:dichloromethane (1:1(v/v), 360 g) and water (40 g) to make a spraying solution. The remaining processes and conditions were the same as in example 2-1.

EXAMPLE 5-4

100 g of itraconazole, 100 g of polyvinylalcohol, 50 g of lactic acid, 30 g of diethylene glycol monoethyl ether (solubilizer), 105 g of sodium starch glycolate and 105 g of colloidal silica were mixed to make a mixture containing itraconazole.

EXAMPLE 6

Evaluating the Effect of Lactic Acid when Using Diethylaminoacetate as a Polymer

EXAMPLE 6-1

100 g of itraconazole and 100 g of diethylaminoacetate (polymer) were dissolved in ethanol:dichloromethane (1:1 (v/v), 1,200 g) to make a spraying solution. The remaining processes and conditions were the same as in example 2-1.

EXAMPLE 6-2

100 g of itraconazole, 100 g of diethylaminoacetate and 50 g of lactic acid were dissolved in a mixture of ethanol:dichloromethane (1:1(v/v), 360 g) and water (40 g) to make a spraying solution. The remaining processes and conditions were the same as in example 2-1.

EXAMPLE 6-3

100 g of itraconazole, 100 g of diethylaminoacetate, 50 g of lactic acid and 30 g of diethylene glycol monoethyl ether (solubilizer) were dissolved in a mixture of ethanol:dichloromethane (1:1(v/v), 360 g) and water (40 g) to make a spraying solution. The remaining processes and conditions were the same as in example 2-1.

EXAMPLE 6-4

100 g of itraconazole, 100 g of diethylaminoacetate, 50 g of lactic acid, 30 g of diethylene glycol monoethyl ether (solubilizer), 105 g of sodium starch glycolate and 105 g of colloidal silica were mixed to make a mixture containing itraconazole.

The ingredients and their amounts of itraconazole-containing preparations prepared in example 2-1 to example 6-4 described above were summarized in table 2.

TABLE 2

|  |  | Example (g) | | | | | | | | | |
|---|---|---|---|---|---|---|---|---|---|---|---|
|  |  | 2-1 | 2-2 | 2-3 | 2-4 | 3-1 | 3-2 | 3-3 | 3-4 | 4-1 | 4-2 |
| drug | itraconazole | 100 | 100 | 100 | 100 | 100 | 100 | 100 | 100 | 100 | 100 |
| polymer | AAMC | 100 | 100 | 100 | 100 |  |  |  |  |  |  |
|  | HPMC |  |  |  |  | 100 | 100 | 100 | 100 |  |  |
|  | PVP |  |  |  |  |  |  |  |  | 100 | 100 |
|  | PVA |  |  |  |  |  |  |  |  |  |  |
|  | DEAA |  |  |  |  |  |  |  |  |  |  |
| acid | Lactic acid |  | 50 | 50 | 50 |  | 50 | 50 | 50 |  | 50 |
| solubilizer | Transcutol ™ |  |  | 30 | 30 |  |  | 30 | 30 |  |  |
|  | solvent amount (liter) | 1.2 | 0.4 | 0.4 | — | 1.2 | 0.4 | 0.4 | — | 1.2 | 0.4 |

|  |  | Example (g) | | | | | | | | | |
|---|---|---|---|---|---|---|---|---|---|---|---|
|  |  | 4-3 | 4-4 | 5-1 | 5-2 | 5-3 | 5-4 | 6-1 | 6-2 | 6-3 | 6-4 |
| drug | itraconazole | 100 | 100 | 100 | 100 | 100 | 100 | 100 | 100 | 100 | 100 |
| polymer | AAMC |  |  |  |  |  |  |  |  |  |  |
|  | HPMC |  |  |  |  |  |  |  |  |  |  |
|  | PVP | 100 | 100 |  |  |  |  |  |  |  |  |
|  | PVA |  |  | 100 | 100 | 100 | 100 |  |  |  |  |
|  | DEAA |  |  |  |  |  |  | 100 | 100 | 100 | 100 |
| acid | Lactic acid | 50 | 50 |  | 50 | 50 | 50 |  | 50 | 50 | 50 |
| solubilizer | Transcutol ™ | 30 | 30 |  |  | 30 | 30 |  |  | 30 | 30 |
|  | solvent amount (liter) | 0.4 | — | 1.2 | 0.4 | 0.4 | — | 1.2 | 0.4 | 0.4 | — |

In table 2, AAMC, HPMC, PVP, PVA and DEAA mean aminoalkylmethacrylate copolymer, hydroxypropylmethylcellulose, polyvinylpyrrolidone, polyvinylalcohol and diethylaminoacetate, respectively.

EXAMPLE 7

Using a Spray-Dryer

The itraconazole-containing solid dispersions prepared using a spray-dryer showed more regular and smaller particles than using the fluidized bed granulator, but the dissolution pattern of the solid dispersions made with the spray-dryer was similar to that of the roughly pulverized solid dispersions made with the fluidized bed granulator.

EXAMPLE 7-1

100 g of itraconazole, 90 g of aminoalkylmethacrylate copolymer (polymer), 50 g of lactic acid and 30 g of diethylene glycol monoethyl ether (solubilizer) were dissolved in a mixture of ethanol:dichloromethane (1:1(v/v), 450 g) and water (50 g), and then 5 g of talc was dispersed regularly in the solution. The solution was then sprayed and dried using a spray-dryer (Buchi 190 mini spray dryer) to make an itraconazole-containing solid dispersion. Spraying conditions were as follows: spraying velocity 15-30 □/min, spray-drying pressure 2-4.5 kg/□, inlet air temperature 90-120° C. and outlet air temperature 40-80° C.

EXAMPLE 7-2

100 g of itraconazole, 90 g of hydroxyproypmethylcellulose (polymer), 50 g of lactic acid and 30 g of diethylene glycol monoethyl ether (solubilizer) were dissolved in a mixture of ethanol:dichloromethane (1:1(v/v), 450 g) and water (50 g), and then 5 g of talc was dispersed regularly in the solution. The remaining processes and conditions were the same as in example 7-1.

EXAMPLE 7-3

100 g of itraconazole, 90 g of polyvinylpyrrolidone (polymer), 50 g of lactic acid and 30 g of diethylene glycol monoethyl ether (solubilizer) were dissolved in a mixture of ethanol:dichloromethane (1:1(v/v), 450 g) and water (50 g), and then 5 g of talc was dispersed regularly in the solution. The remaining processes and conditions were the same as in example 7-1.

EXAMPLE 7-4

100 g of itraconazole, 90 g of polyvinylalcohol (polymer), 50 g of lactic acid and 30 g of diethylene glycol monoethyl ether (solubilizer) were dissolved in a mixture of ethanol: dichloromethane (1:1(v/v), 450 g) and water (50 g), and then 5 g of talc was dispersed regularly in the solution. The remaining processes and conditions were the same as in example 7-1.

EXAMPLE 7-5

100 g of itraconazole, 90 g of diethylaminoacetate (polymer), 50 g of lactic acid and 30 g of diethylene glycol monoethyl ether (solubilizer) were dissolved in a mixture of ethanol:dichloromethane (1:1(v/v), 450 g) and water (50 g), and then 5 g of talc was dispersed regularly in the solution. The remaining processes and conditions were the same as in example 7-1.

Itraconazole-containing capsules or tablets were prepared with solid dispersions of example 2-1 to example 7-5 and pharmaceutically acceptable excipients like diluent, disintegrator, lubricant and so on.

EXPERIMENTAL EXAMPLE 2

Itraconazole-containing capsules (containing 100 mg of itraconazole in 450 mg of the total contents) were prepared with solid dispersions of example 2-1 to example 7-5 and a mixture (3:1, w/w) of sodium starch glycolate and colloidal silica, and then subjected to dissolution tests using media having different pH like experimental example 1. Commercially available products containing 100 mg of itraconazole, Sporanox™ tablet and Sporanox™ capsule, were used as control. Results are shown in table 3.

TABLE 3

| Example (%) | pH 1.2 | pH 2.4 | pH 3.0 |
|---|---|---|---|
| Itraconazole | 3.9 | 0.3 | 0.1 |
| Sporanox capsule | 66.4 | 6.1 | 1.4 |
| Sporanox tablet | 69.2 | 5.9 | 1.1 |
| Example 2-1 | 91.0 | 77.3 | 48.6 |
| Example 2-2 | 98.3 | 95.8 | 89.7 |
| Example 2-3 | 98.0 | 96.2 | 88.8 |
| Example 2-4 | 7.6 | 1.2 | 0.3 |
| Example 3-1 | 87.4 | 32.6 | 19.5 |
| Example 3-2 | 92.1 | 57.8 | 52.5 |
| Example 3-3 | 92.8 | 67.0 | 62.3 |
| Example 3-4 | 6.3 | 2.1 | 0.2 |
| Example 4-1 | 77.4 | 7.2 | 5.2 |
| Example 4-2 | 87.4 | 35.6 | 26.3 |
| Example 4-3 | 92.3 | 55.0 | 48.2 |
| Example 4-4 | 7.1 | 0.9 | 0.2 |
| Example 5-1 | 72.5 | 4.5 | 3.1 |
| Example 5-2 | 80.2 | 21.6 | 13.2 |
| Example 5-3 | 88.7 | 43.4 | 27.8 |
| Example 5-4 | 5.6 | 1.9 | 0.1 |
| Example 6-1 | 90.7 | 90.3 | 80.1 |
| Example 6-2 | 93.8 | 91.2 | 85.4 |
| Example 6-3 | 96.2 | 90.5 | 89.8 |
| Example 6-4 | 8.2 | 2.3 | 0.7 |
| Example 7-1 | 98.7 | 95.2 | 85.9 |
| Example 7-2 | 90.0 | 78.3 | 69.5 |
| Example 7-3 | 92.6 | 58.7 | 47.7 |
| Example 7-4 | 85.5 | 62.8 | 33.4 |
| Example 7-5 | 94.9 | 82.0 | 70.0 |

As shown in table 3, solid dispersions of the present invention showed much higher dissolution rates in pH 2.4 and 3.0 as well as pH 1.2 medium than itraconazole, Spranox™ tablet and Spranox™ capsule, and there was not any difference between solid dispersions made by the fluidized bed granulator and solid dispersions made by the spray-dryer. Furthermore, examples 2-4, 3-4, 4-4, 5-4 and 6-4 (physical mixtures of itraconazole, polymer, lactic acid and solubilizer) did not show any improvement of dissolution rate in all three dissolution media. This means that polymer, lactic acid and solubilizer of a physical mixture can not increase solubility of itraconazole both alone and combination, and the formation of solid dispersion is important in improving solubility and dissolution rate.

Adding a solubilizer is more effective in case using a pH-independent polymer (hydroxypropylmethylcellulose, polyvinylpyrrolidone and polyvinylalcohol) than a pH-dependent polymer (aminoalkylmethacrylate and diethylaminoacetate).

From the above results, it is expected that the itraconazole-containing solid dispersions of the present invention can exhibit the much increased bioavailability and the much decreased absorption variation in inter- and intra-individuals when compared with commercially available products, Sporanox™ tablet and Sporanox™ capsule.

EXAMPLE 3

Effect of Particle Size of a Solid Dispersion Containing Itraconazole

Itraconazole-containing solid dispersions prepared in example 2-3, 3-3, 4-3, 5-3, 6-3, 7-1, 7-2, 7-3, 7-4 and 7-5 were grouped respectively by being passed through a 30 mesh and 60 mesh sieve, and were subjected to dissolution tests without adding a pharmaceutically acceptable excipient. Sporanox™ capsule was used as a control, and the method was the same as in experimental example 2. Results were shown in table 4.

TABLE 4

| Example (%) | | pH 1.2 | pH 2.4 | pH 3.0 |
|---|---|---|---|---|
| Sporanox capsule | with capsule shell | 66.4 | 6.1 | 1.4 |
| | without capsule shell | 68.1 | 5.9 | 1.5 |
| Example 2-3 | mesh 35-mesh 60 | 98.5 | 95.7 | 89.0 |
| | pass mesh 60 | 98.5 | 95.9 | 88.5 |
| Example 3-3 | mesh 35-mesh 60 | 92.1 | 52.0 | 45.9 |
| | pass mesh 60 | 92.7 | 53.3 | 46.0 |
| Example 4-3 | mesh 35-mesh 60 | 93.5 | 56.7 | 41.5 |
| | pass mesh 60 | 94.2 | 57.2 | 42.7 |

TABLE 4-continued

| Example (%) | | pH 1.2 | pH 2.4 | pH 3.0 |
|---|---|---|---|---|
| Example 7-1 | mesh 35-mesh 60 | 98.0 | 93.6 | 87.8 |
| | pass mesh 60 | 99.2 | 94.1 | 87.0 |
| Example 7-2 | mesh 35-mesh 60 | 88.3 | 75.4 | 66.2 |
| | pass mesh 60 | 88.0 | 76.3 | 67.8 |
| Example 7-3 | mesh 35-mesh 60 | 91.4 | 58.7 | 48.8 |
| | pass mesh 60 | 92.0 | 59.0 | 42.7 |
| Example 7-4 | mesh 35-mesh 60 | 85.3 | 61.9 | 35.6 |
| | pass mesh 60 | 86.1 | 63.3 | 33.3 |
| Example 7-5 | mesh 35-mesh 60 | 95.8 | 84.7 | 72.3 |
| | pass mesh 60 | 97.2 | 85.9 | 75.7 |

As shown in table 4, the particle sizes of the solid dispersions made by the spray-dryer or fluidized bed granulator did not have significant effects on dissolution rates. This means that itraconazole, polymer and lactic acid were dissolved uniformly in the spray-drying solution and the uniformity was maintained during drying process.

EXPERIMENTAL EXAMPLE 4

Stability Test

Stability test was performed for eight weeks on the basis of dissolution rates evaluated in experimental example 2. Changes of appearance and dissolution rate were evaluated, and change of content was also evaluated. Stability test was performed at an accelerated condition (40° C., 75% RH) and dissolution tests were done like experimental example 2. Results were shown in table 5.

TABLE 5

| | Change of dissolution rate | | | | |
|---|---|---|---|---|---|
| Example | pH 1.2 | pH 2.4 | pH 3.0 | Content | Appearance |
| Itraconazole | −5.5 | −3.7 | −3.7 | 99.8 | not changed |
| Sporanox capsule | −15.3 | −11.6 | −3.0 | 99.9 | not changed |
| Sporanox tablet | −19.6 | −7.5 | −5.3 | 100.1 | not changed |
| Example 2-1 | −12.1 | −5.0 | −2.8 | 99.4 | agglomerated after 2 weeks |
| Example 2-2 | −7.9 | −2.5 | −3.4 | 99.3 | low flowability after 7 weeks |
| Example 2-3 | −3.7 | −3.0 | −1.1 | 99.7 | low flowability after 5 weeks |
| Example 2-4 | −4.3 | −3.8 | −1.9 | 99.9 | not changed |
| Example 3-1 | −30.7 | −21.5 | −13.4 | 100.0 | agglomerated after 10 days |
| Example 3-2 | −11.9 | −10.2 | −5.7 | 99.1 | agglomerated after 7 weeks |
| Example 3-3 | −8.0 | −5.9 | −5.0 | 99.3 | agglomerated after 5 weeks |
| Example 3-4 | −6.6 | −7.2 | −3.4 | 99.3 | low flowability after 6 weeks |
| Example 4-1 | −26.6 | −12.6 | −8.4 | 99.0 | agglomerated after 2 weeks |
| Example 4-2 | −10.8 | −10.0 | −4.9 | 98.0 | agglomerated after 6 weeks |
| Example 4-3 | −7.3 | −5.2 | −2.8 | 98.3 | agglomerated after 4 weeks |
| Example 4-4 | −7.1 | −4.9 | −5.0 | 99.4 | low flowability after 7 weeks |
| Example 5-1 | −32.6 | −25.6 | −21.2 | 98.1 | agglomerated after 1 week |
| Example 5-2 | −23.4 | −15.7 | −10.3 | 99.4 | agglomerated after 5 weeks |
| Example 5-3 | −15.0 | −13.5 | −7.5 | 99.1 | agglomerated after 4 weeks |
| Example 5-4 | −5.2 | −6.0 | −4.3 | 98.7 | low flowability after 7 weeks |
| Example 6-1 | −14.8 | −6.3 | −3.3 | 98.7 | agglomerated after 2 weeks |
| Example 6-2 | −8.8 | −4.1 | −3.3 | 99.0 | low flowability after 7 weeks |
| Example 6-3 | −5.6 | −5.0 | −2.0 | 98.8 | low flowability after 5 weeks |
| Example 6-4 | −5..1 | −5.2 | −4.7 | 99.6 | not changed |
| Example 7-1 | −6.5 | −7.3 | −2.7 | 99.5 | low flowability after 4 weeks |
| Example 7-2 | −9.2 | −6.4 | −6.0 | 99.8 | low flowability after 3 weeks |
| Example 7-3 | −11.0 | −10.2 | −8.1 | 98.3 | low flowability after 3 weeks |
| Example 7-4 | −12.6 | −5.7 | −6.8 | 99.0 | low flowability after 3 weeks |
| Example 7-5 | −7.3 | −4.0 | −2.7 | 99.9 | low flowability after 4 weeks |

TABLE 4-continued

| Example (%) | | pH 1.2 | pH 2.4 | pH 3.0 |
|---|---|---|---|---|
| Example 5-3 | mesh 35-mesh 60 | 89.8 | 44.6 | 30.3 |
| | pass mesh 60 | 91.3 | 45.9 | 31.6 |
| Example 6-3 | mesh 35-mesh 60 | 97.7 | 91.5 | 88.4 |
| | pass mesh 60 | 98.5 | 90.3 | 86.2 |

As shown in table 5, the present inventors could evaluate the effect of lactic acid and solubilizer on the stability of dissolution rate of the solid dispersion during the stability test. A lowering of free flowability is a preliminary stage of agglomeration and suggests the degree of change in accordance with intake of water. Appearances of solid dispersions of example 2-2, 3-2, 4-2, 5-2 and 6-2 comprising lactic acid were little changed when compared with other compositions, and dissolution rates of solid dispersions further comprising the solubilizer were the least changed.

Contents of almost solid dispersions have little changed. The lowering of dissolution rate over time means that itraconazole in composition changes from amorphous to crystal form. Lactic acid in the solid dispersion is expected to absorb water before other ingredients absorb it in an accelerated condition, so that it prevents the change of itraconazole from amorphous to crystal form.

Low decrease of itraconazole dissolution rate in physical mixtures of example 2-4, 3-4, 4-4, 5-4 and 6-4 is because the initial dissolution rates of them are very low. That is, it means that almost itraconazole in physical mixtures before stability test are already crystal form.

EXAMPLE 8

Evaluating the Effect of Amount of Aminoalkylmethacrylate Copolymer Based on the Weight of Itraconazole Itraconazole-containing solid dispersions were made with 100 g of itraconazole, 50 g of lactic acid and aminoalkylmethacrylate copolymer (polymer) having the amount shown in table 6 according to the same method as in example 2-2.

EXAMPLE 9

Evaluating the Effect of Amount of Polyvinylpyrrolidone Based on the Weight of Itraconazole Itraconazole-containing solid dispersions were made with 100 g of itraconazole, 50 g of lactic acid, 30 g of diethylene glycol monoethyl ether (solubilizer), 5 g of talc and polyvinylpyrrolidone (polymer) having the amount shown in table 7 according to the same method as in example 7-3.

EXPERIMENTAL EXAMPLE 5

Evaluation of Solid Dispersions Made in Example 8 and 9

Itraconazole-containing solid dispersions made in example 8 and 9 were subjected to dissolution test like experimental example 2. Results were shown in table 6 and 7, respectively.

TABLE 6

| Example (%) | Amount of aminoalkylmethacrylate copolymer (g) | pH 1.2 | pH 2.4 | pH 3.0 |
|---|---|---|---|---|
| Itraconazole | — | 3.9 | 0.3 | 0.1 |
| Example 8-1 | 70 | 82.9 | 75.8 | 55.0 |
| Example 8-2 | 90 | 93.7 | 83.1 | 72.4 |
| Example 8-3 | 100 | 98.3 | 95.8 | 89.7 |
| Example 8-4 | 200 | 90.3 | 82.2 | 75.3 |
| Example 8-5 | 300 | 75.5 | 64.1 | 45.6 |

TABLE 7

| Example (%) | Amount of polyvinylpyrrolidone (g) | pH 1.2 | pH 2.4 | pH 3.0 |
|---|---|---|---|---|
| Itraconazole | — | 3.9 | 0.3 | 0.1 |
| Example 9-1 | 70 | 90.5 | 56.8 | 37.2 |

TABLE 7-continued

| Example (%) | Amount of polyvinylpyrrolidone (g) | pH 1.2 | pH 2.4 | pH 3.0 |
|---|---|---|---|---|
| Example 9-2 | 90 | 91.7 | 55.0 | 40.4 |
| Example 9-3 | 100 | 92.6 | 58.7 | 47.7 |
| Example 9-4 | 200 | 83.0 | 42.1 | 31.3 |
| Example 9-5 | 300 | 72.3 | 40.5 | 25.1 |

As shown in table 6 and 7, the solid dispersion of the present invention can maintain the improved dissolution rate within some range of the amount of polymer used based on the weight of itraconazole. However, example 8-5 and 9-5 showed the decreased dissolution rates, which are thought to be due to the high viscosity of the polymer.

EXAMPLE 10-1

100 g of itraconazole, 90 g of aminoalkylmethacrylate copolymer (polymer) and 50 g of lactic acid were dissolved in a mixture of ethanol:dichloromethane (1:1(v/v), 360 g) and water (40 g) to make a spraying solution. An itraconazole-containing solid dispersion was made by the same process and method as in example 2-2.

EXAMPLE 10-2

100 g of itraconazole, 90 g of aminoalkylmethacrylate copolymer (polymer), 50 g of lactic acid and 5 g of citric acid were dissolved in a mixture of ethanol:dichloromethane (1:1(v/v), 360 g) and water (40 g) to make a spraying solution. An itraconazole-containing solid dispersion was made by the same process and method as in example 2-2.

EXPERIMENTAL EXAMPLE 6

Capsules containing 100 mg of itraconazole were made with the solid dispersions made in example 10-1 and 10-2 according to the same method as in example 2, and were subjected to dissolution test like experimental example 2.

Dissolution rates of the capsules using the solid dispersions of example 10-1 and 10-2 were 93.7% and 93.1% (pH 1.2), 84.5% and 81.7% (pH 2.4), and 73.9% and 70.4% (pH 3.0), respectively. The dissolution rates of example 10-2 were a little lower than those of example 10-1, whereas the solid dispersion of example 10-2 showed a better handling property (for example, free flowability) than that of example 10-1.

EXPERIMENTAL EXAMPLE 7

Evaluation of Relative Bioavailability

The pharmacokinetic difference between the solid dispersion made in example 2-3 and a commercially available itraconazole preparation (Sporanox™, Janssen) was evaluated. Male white rats (Sprague-Dawley, 13 weeks old, each group has ten rats) were used as test animal. Test animals were acclimated to a new environment for 1 week, and then grouped randomly as control group and test group. Rats were fasted for 48 hours before the testing, and test samples and controls were administered. Catheter for blood-gathering was connected to each rat before the testing.

The solid dispersion of the present invention and the commercially available product were administered orally in an amount of 20 mg itraconazole per kg to test group and control group, respectively. Blood was then collected from the catheter at immediately before the administration, 2, 4, 6, 8, 12 and 24 hours after the administration. Blood analysis was performed with High Performance Liquid Chromatography (HPLC, Shisheido, Japan). 500 µl of plasma was added to the same volume of a pretreatment mobile phase (50 mM phosphate buffer solution:acetonitrile=7.5:2.5), and then the mixture was centrifuged and then filtered with 0.2 µm membrane filter. 100 µl of the filtered solution was injected to HPLC. The pretreatment mobile phase was at a flow rate of 1.0 ml/min, and a mixture (37:63) of 25 mM phosphate buffer solution and acetonitrile was used as a analysis mobile phase. Flow rate of the analysis mobile phase and detection absorbance wavelength were 0.1 mL/min and 258 nm, respectively. Result was shown in FIG. 1.

As shown in FIG. 1, the itraconazole-containing solid dispersion of the present invention showed much higher bioavailability than the commercially available product.

The invention claimed is:

1. A method for improving the dissolution rate of an itraconazole-containing solid dispersion, said method comprising:
    dissolving itraconazole, polymer and lactic acid into a solvent to thereby prepare a solution; and drying the solution, thereby
    preparing said itraconazole-containing solid dispersion, wherein the itraconazole is present in the solid dispersion in an amorphous form, and
    wherein the polymer is at least one selected from the group consisting of hydroxyalkylcellulose, polyalkene oxide, polyethylene-polypropylene copolymer, polyoxyethylene-polyoxypropylene copolymer, polyvinylalcohol, polyvinylpyrrolidone, diethylaminoacetate, and aminoalkylmethacrylate copolymer, and
    wherein the polymer is used in the range of 0.4-3 parts by weight based on the 1 part by weight of itraconazole,
    wherein the lactic acid is used in the range of 0.2-5 parts by weight based on the 1 part by weight of itraconazole,
    wherein the solution is prepared with both water and at least one solvent selected from the group consisting of, dichloromethane, ethanol, methanol, chloroform, and acetone,
    wherein the water is used at a weight of between 1 and 20 (w/w) % by the weight of the total solvent,
    wherein the method does not use phosphoric acid.

2. The method of claim 1 wherein the solution further comprises a solubilizer.

3. The method of claim 2 wherein the solubilizer is used in the range of 0.1-3 parts by weight based on the 1 part by weight of itraconazole.

4. The method of claim 1 wherein the solution further comprises a solid-phase acid.

5. The method of claim 4 wherein the solid-phase acid is at least one selected from the group consisting of citric acid, tartaric acid, maleic acid and succinic acid.

6. The method of claim 1 wherein the water is used at a weight of between 2 and 15 (w/w) % by the weight of the total solvent.

* * * * *